United States Patent [19]

Nardella et al.

[11] Patent Number: 5,417,687
[45] Date of Patent: May 23, 1995

[54] BIPOLAR ELECTROSURGICAL TROCAR

[75] Inventors: Paul C. Nardella, North Easton, Mass.; David C. Yates, West Chester, Ohio

[73] Assignees: Medical Scientific, Inc., Taunton, Mass.; Ethicon Endo-Surgery, Inc., Cincinnati, Ohio

[21] Appl. No.: 55,826

[22] Filed: Apr. 30, 1993

[51] Int. Cl.⁶ .............................................. A61N 5/06
[52] U.S. Cl. ...................................... 606/32; 606/45; 606/29; 606/48; 604/164
[58] Field of Search ............... 606/167, 184, 185, 32, 606/37, 39, 45, 48, 28, 29; 604/164

[56] References Cited

U.S. PATENT DOCUMENTS

| | | |
|---|---|---|
| 3,595,239 | 7/1971 | Petersen .................... 606/45 |
| 3,601,126 | 8/1971 | Estes . |
| 3,913,583 | 10/1975 | Bross . |
| 4,043,342 | 8/1977 | Morrison, Jr. . |
| 4,114,623 | 9/1978 | Meinke et al. . |
| 4,126,137 | 11/1978 | Archibald . |
| 4,418,692 | 12/1983 | Guay . |
| 4,535,773 | 8/1985 | Yoon . |
| 4,651,280 | 3/1987 | Chang et al. . |
| 4,716,897 | 1/1988 | Noguchi et al. . |
| 4,823,791 | 4/1989 | D'Amelio et al. . |
| 4,862,889 | 9/1989 | Feucht . |
| 4,919,129 | 4/1990 | Weber, Jr. et al. ............ 606/45 X |
| 5,009,656 | 4/1991 | Reimels . |
| 5,030,206 | 7/1991 | Lander . |
| 5,089,002 | 2/1992 | Kirwan .................. 606/45 X |
| 5,221,281 | 6/1993 | Klicek . |

FOREIGN PATENT DOCUMENTS

| | | |
|---|---|---|
| 0479482A1 | 9/1991 | European Pat. Off. . |
| 0508453A1 | 4/1992 | European Pat. Off. . |
| WO14514 | 2/1992 | WIPO .................. 606/45 |
| WO92/14514 | 9/1992 | WIPO . |

Primary Examiner—Peter A. Aschenbrenner
Attorney, Agent, or Firm—Lahive & Cockfield; William C. Geary, III

[57] ABSTRACT

The invention provides an electrosurgical tissue penetrating probe (e.g., a trocar) for use with surgical procedures such as a laproscopy. The trocar has a stylet disposed within the housing member, having an active electrode disposed on a distal end thereof to deliver electrosurgical energy to the target tissue in contact with the stylet. A return electrode is disposed on the housing member to form part of a return electrical path to the delivery electrosurgical energy. The invention also provides an electrosurgical trocar system having an impedance monitor and associated power regulating circuitry to control the amount of electrosurgical energy delivered to tissue so that the measured tissue impedance is maintained within a preselected range.

7 Claims, 2 Drawing Sheets

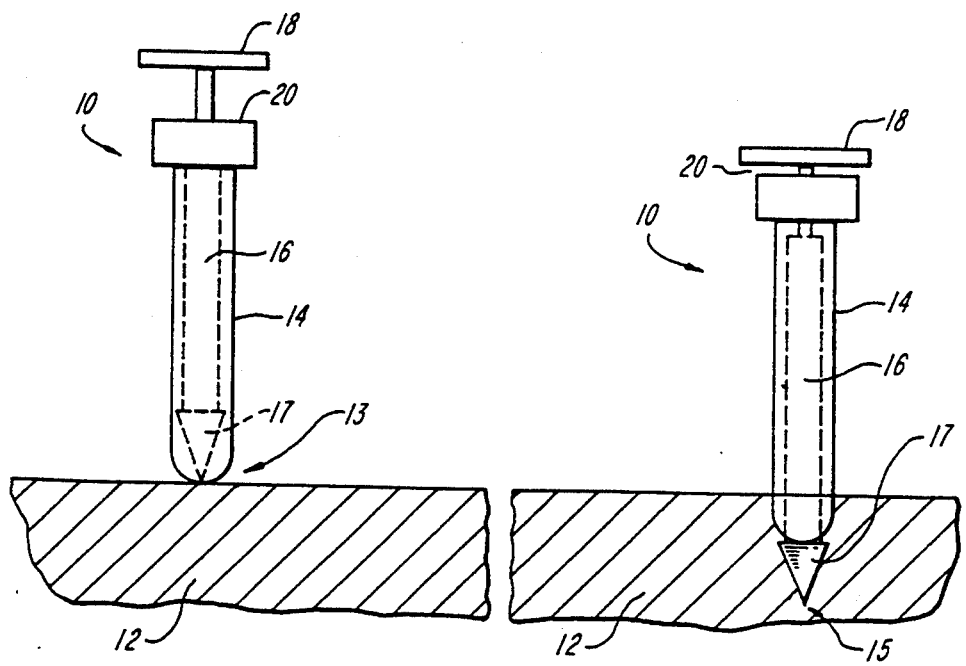
FIG. 1A
(PRIOR ART)
FIG. 1B
(PRIOR ART)
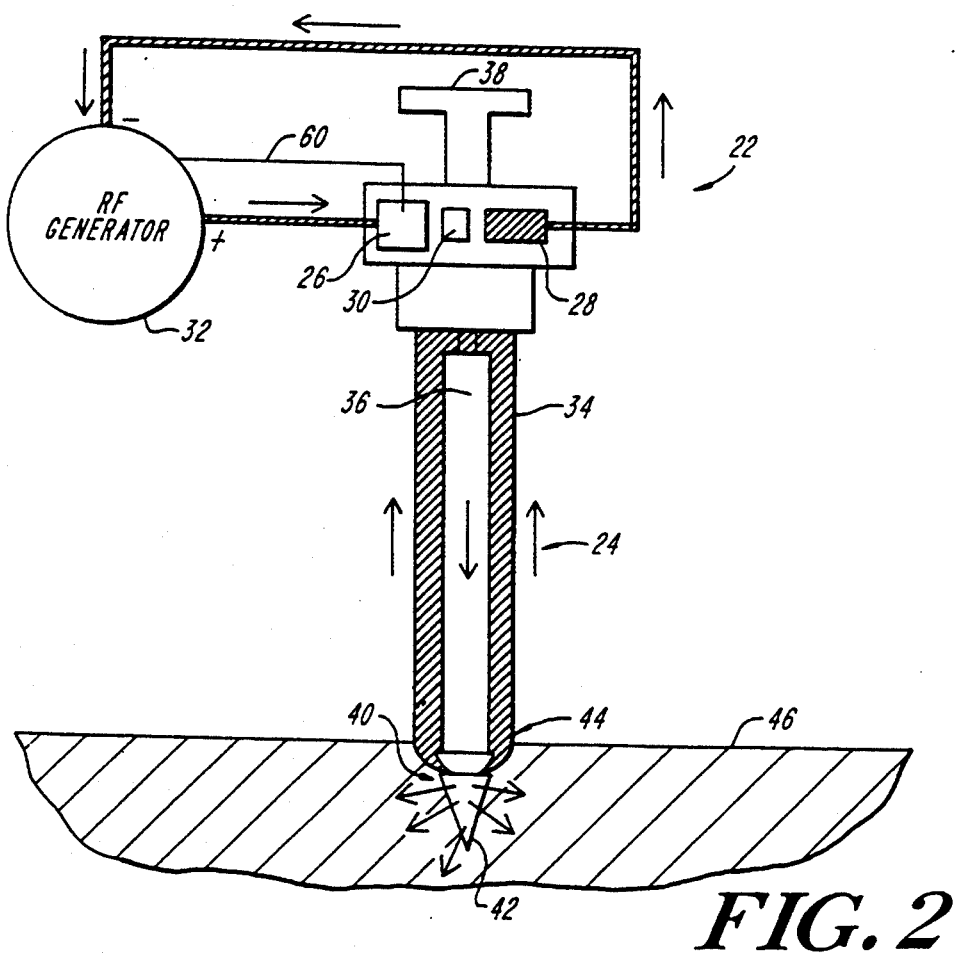
FIG. 2

BIPOLAR ELECTROSURGICAL TROCAR

BACKGROUND OF THE INVENTION

This invention relates generally to a bipolar electrosurgical device, such as a trocar, for penetrating tissue.

Tissue penetrating probes, such as trocars and insufflation needles, are well known. A trocar typically includes an elongate stylet having a sharp, pointed obturator tip, disposed within a sheath or sleeve, and a handle portion that controls reciprocation of the stylet. A user of the trocar grips the handle and applies force such that the sharp tip of stylet penetrates tissue to a desired depth. A common use of the trocar is to gain access to the abdominal cavity for subsequent surgical purposes. This is typically accomplished by penetrating the abdomen with the tip of the stylet, removing the stylet from the sheath, and leaving the sheath within the abdominal wall to serve as a conduit to facilitate surgical procedures or inspections.

Insufflation needles are known devices, smaller in diameter than trocars, that also enable penetration of the abdominal wall. These often are used to insufflate the abdominal cavity before a larger opening is made with a trocar.

Electrosurgical energy, typically in the radio frequency range, has been used to enhance surgical procedures. Surgical tools utilizing electrosurgical energy are disclosed in U.S. patent application Ser. No. 786,572, filed on Nov. 1, 1991, and U.S. patent application Ser. No. 005,600, filed on Jan. 19, 1993.

Various monopolar electrosurgical devices also are known. However, monopolar devices are not believed to be the most effective means for applying electrosurgical energy in surgical techniques. Typically, a remote ground pad is placed on the patient to form the negative pole in the electrosurgical circuit. The energy applied through the electrosurgical instrument must often traverse significant distances through the patient's body before reaching the return electrode. This can lead to ineffective control in applying the optimal mount of energy. In some instances patient burning can also result due to poor contact of the ground pad or ineffective control of energy delivery.

A trocar that uses electrosurgical energy is described in International Application No. WO/92/14514. The trocar can be monopolar or bipolar. In the monopolar mode the obturator tip of the trocar serves as the active electrode while a remote ground pad serves as the return electrode. In the bipolar mode the obturator tip has two separate, insulted elements (foraging a "duckbill" shape), each of which serves as one of the poles. Although this form of the trocar is bipolar in the sense that it forms both poles in circuit, it does so on the single cutting element and does not simultaneously function as a traditional trocar.

Despite existing technology applied to electrosurgical trocars, there remains a need for an effective bipolar trocar able to safely utilize electrosurgical energy to assist in penetrating and cauterizing tissue.

Accordingly, an object of the invention is to provide a bipolar tissue penetrating probe that uses electrosurgical energy to enhance tissue penetration and to cauterize tissue simultaneous with tissue penetration. Another object is to provide a bipolar trocar device able to penetrate and to cauterize tissue simultaneously. A further object of the invention is to provide such a device that enables more effective use of electrosurgical energy to penetrate and cauterize tissue. These and other objects of the invention will be evident from the disclosure that follows.

SUMMARY OF THE INVENTION

The invention comprises a bipolar electrosurgical probe that simultaneously penetrates and cauterizes tissue. The probe preferably is a trocar, but can also take the form of other probes such as insufflation needles.

The electrosurgical trocar of the invention comprises a stylet disposed within a hollow housing or sheath member. The stylet includes a sharpened tissue penetrating obturator tip at its distal end and a handle, for manipulating the trocar, at its proximal end. The trocar further includes an active electrode formed by or on the tissue-penetrating obturator tip, and a return electrode formed by or disposed on a tissue contacting portion of the sheath member. Separate current communication lines connect between an external power source and the active and return electrodes.

The stylet further is adapted to reciprocate within the housing member, such that it can protrude from the open distal end of the housing member and retract within the housing. The trocar handle, mounted adjacent the proximal end of the housing member, is used both to manipulate the trocar and to control any axial displacement of the stylet.

In operation, the trocar is placed in contact with tissue and electrosurgical energy is delivered from an external source generator to the active electrode formed by the tissue penetrating distal tip of the stylet as tissue penetration is effected. The tissue penetrating tip of the stylet, which serves as the active electrode, is electrically isolated from the return electrode mounted on the housing member. The active electrode (i.e. the edge) utilizes electrosurgical energy to assist in cutting and cauterizing tissue. The return electrode, as noted above, serves as a ground.

In another aspect, the electrosurgical energy applied to the tissue can be regulated by monitoring tissue impedance. Once the tissue impedance is known, the generated electrosurgical energy can be regulated so that the current and voltage will change within the electrosurgical circuit to maintain a tissue impedance to within a preselected range. The energy delivered to the active electrode can be shutdown, in another aspect, if the measured impedance is outside a preselected range or exceeds a preselected value.

Although the invention is primarily disclosed with respect to a bipolar trocar, the invention also relates to other bipolar tissue penetrating probes such as insufflation needles.

These and other aspects will be apparent from the following description, where the invention is described and illustrated in connection with certain preferred embodiments. However, it should be clear that various additions, subtractions, and modifications can be made by those skilled in the art without departing from the scope of the invention.

BRIEF DESCRIPTION OF THE DRAWINGS

FIG. 1 schematically illustrates a prior art trocar before and after tissue penetration.

FIG. 2 schematically illustrates an electrosurgical trocar system constructed according to the present invention.

DETAILED DESCRIPTION OF THE INVENTION

Figure 3:
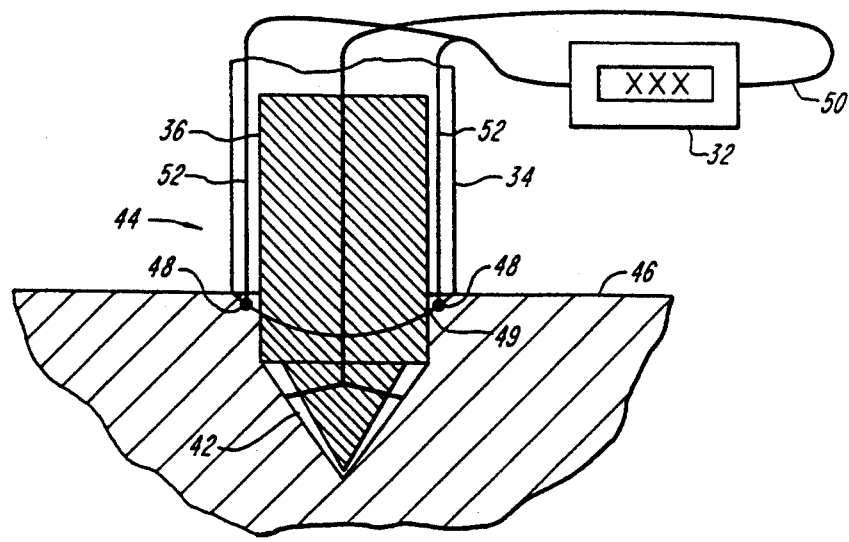
FIG. 3 schematically illustrates a distal end of a trocar of the type illustrated in FIG. 2.

FIG. 1 illustrates a prior art trocar 10 prior to (A) and after (B) penetrating tissue 12. In configuration A, the trocar 10 is simply in contact with the tissue 12 at a surface location 13. In configuration B, the trocar 10 has penetrated tissue 12 to a depth 15 by extending the distal, pointed end 17 of the stylet from within the housing member into the tissue 12.

The prior art trocar 10 as illustrated has an outer housing member 14 and an inner stylet 16 which can be axially displaced within the housing 14. A handle 18 is disposed at proximal end 20 of the trocar and is used to both control the trocar and to axially drive the stylet 16 out of the distal end of the housing member 14.

FIG. 2 illustrates a bipolar electrosurgical trocar system 22 constructed according to the invention. As illustrated, system 22 comprises an electrosurgical trocar 24 which preferably includes a power control module 26, an impedance monitor 28 and an activation switch 30. The power control module 26 and impedance monitor 28 are in communication with a source of electrosurgical energy such as RF generator 32.

The trocar 24 includes an elongate, hollow housing or sheath 34 within which is disposed an elongate stylet 36. Preferably a handle 38 is mounted at a proximal portion of the trocar and is secured to a proximal end of the stylet 36 to facilitate axial movement of the stylet such that its distal tip 40 may be retracted within the sheath 34 and extended beyond sheath 34. The distal end 40 of the stylet comprises a sharp obturator tip 42 that is adapted to penetrate tissue when extended from the distal end of sheath 34. Preferably, the distal end of sheath 34 includes an opening that enables at least a portion of the obturator tip 42 to extend therefrom, but which prevents the entire stylet 36 from passing through the opening.

It should be clear to those skilled in the art that the system 22 is illustrative rather than limiting. For example, the power control module 26, impedance monitor 28, and activation switch 30 can be configured external to the remainder of the trocar 24, for example at the RF generator 32. Accordingly, a trocar constructed in accordance with the invention can comprise an electrosurgical trocar which is adaptable to external electronics, for example one with current communication lines disposed with the trocar to electrically connect the electrodes and to one or more electronic devices. Alternatively, one of ordinary skill in the art will appreciate that the trocar 24 can be constructed to have a generator unit and the associated electronics mounted upon the trocar itself.

FIG. 3 illustrates a distal portion 44 of a trocar device constructed in accordance with the invention, for example for use with the trocar 24 illustrated in FIG. 2. As illustrated, the distal portion 44 of trocar 24 is configured as a bipolar electrosurgical instrument adapted to apply electrosurgical energy to tissue 46. Obturator tip 42 preferably serves as an active, energy delivering electrode such that tissue penetration is enhanced and cauterization is achieved by the delivery of electrosurgical energy from obturator tip 42 to tissue 46. Preferably, one or more electrodes 48 disposed at a lower, tissue contacting portion 49 of sheath 34 serve as return or ground electrodes. The tissue penetrating obturator tip 42 preferably is in electrical contact with a first communication line 50 that communicates with an external power source such as generator 32 to enable the tip 42 to serve as an electrosurgical energy delivering electrode. Similarly, second communication line 52 is in circuit with the return electrodes 48 to provide communication with the ground or negative pole of a power source such as RF generator 32.

The tip 42 can also include a penetrating wire (not shown) extending from the distal end of the device 44. Such a wire preferably is connected electrically to the active electrode at the tissue-penetrating edge 42 and functions to reduce the force of entry required to penetrate tissue. Preferably, in this configuration, only the extreme distal end of the tip 42 would serve as a conductive electrode to deliver energy to tissue. This increases the current density at the distal tip 42 (and extended wire), thus heating only a small portion of a wound. The distance by which penetrating wire extends from tip 42 may vary, but typically is on the order of about 0.5 cm.

During use, the distal tip 44 of the bipolar trocar 24 shown in FIG. 3 forms a part of the circuit used to apply electrosurgical energy to tissue. The tissue-penetrating obturator tip 42 functions as the positive pole of the circuit and the return electrodes 48 function as the negative pole. Thus an external power source, e.g., illustrated as the generator and monitor 32, can be connected to the obturator tip 42 and to the return electrodes 48 to complete the circuit with the tissue 46, thereby forming the bipolar electrosurgical trocar of the invention.

As further shown in FIG. 3, the first communication line 50 may extend from generator 32 through the interior of sheath 34, and terminate at a point on the obturator tip 42. In another embodiment (not illustrated) stylet 36 may be made entirely of a conductive material and line 50 may simply extend from generator 32 and terminate at a proximal portion of the stylet. Stylet 36, as noted above, preferably is made entirely of a conductive material such as surgical grade stainless steel. Alternatively, the stylet can be made of stainless steel, and have a highly conductive material (e.g., gold, silver, or platinum) coated upon the obturator tip 42. In this embodiment it is preferred to have the communication line 50 extend from the generator 32 to the conductive coating of the obturator tip 42.

Sheath 34 preferably is manufactured from a surgically compatible polymeric material of the type known in the art. A distal, tissue contacting portion 49 of sheath 34 preferably includes one or more electrodes 48 positioned so as to contact tissue when obturator tip 42 is in contact with tissue. Electrodes 48 can be point electrodes disposed at a bottom tissue contacting portion 49 of sheath 34 as illustrated in FIG. 3. Alternatively, the electrodes may comprise one or more ring electrodes (not shown) that extend about the outer circumference of the bottom portion 49 of sheath 34. Similarly, the tissue-penetrating obturator tip 42 can form an annulus or cone shaped (not shown) active electrode that extends about the circumference of the tip.

In another embodiment, sheath 34 may be manufactured from or coated with a conductive material. For example, sheath 34 may be made entirely of a conductive material, as long as it is electrically isolated from stylet 36. When the entire sheath is made of a conductive material, it is preferred to apply an insulating material over at least a portion of the outer surface of the sheath 34. Electrodes 48 may also be formed from a conductive coating applied to a distal, tissue contacting surface of sheath 34.

The electrodes 48 communicate with generator 32 through second communication line 52. Communication line 52 preferably extends through the interior of sheath 34, terminating at electrodes 48. If sheath 34 is made entirely of a conductive material communication line 52 need only connect to a proximal portion of sheath 34.

Electrodes 48 are, of course, manufactured from a conductive material suitable for use in surgical applications. Suitable materials include gold, silver, and platinum.

As noted, FIG. 2 illustrates an electrosurgical trocar system 22 constructed in accordance with the invention. The electrosurgical trocar system 22 has a stylet 36 disposed within a sheath member 34. The stylet 36 and sheath 34 together function as the two poles of the system 22 when connected to an RF generator 32. The stylet 36 has a tissue penetrating obturator tip 42 at its distal end which forms the active electrode at the positive pole, while a distal, tissue contacting portion 49 of the sheath member 34 functions as the return electrode or negative pole of the system. In order for the trocar 24 to effectively function as a bipolar surgical instrument it is necessary that the obturator tip 42, serving as the active electrode, be electrically isolated from the return electrode(s) 48.

As further illustrated in FIG. 2, system 22 may also include power control module 26, impedance monitor 28, and activation switch 30. The impedance monitor 28 preferably determines the impedance of tissue 46 by quantifying the applied electrosurgical voltage and current within the circuit of the system 22 when in contact with the tissue 46. The impedance monitor 28 then transmits a signal representative of tissue impedance to the power control module 26 via internal circuitry (not shown). The power control module 26 responds to this signal and further communicates with the RF generator 32 via signal line 60 to regulate the flow of electrosurgical energy to the tissue 46. Preferably, the electrosurgical energy is regulated such that the tissue impedance as measured by impedance monitor 28 remains within a preselected range, such as about 20–500 Ohms. Preferably, the power control module is further arranged to cease the flow of electrosurgical energy to the tip 42 when the measured impedance changes significantly or is outside the preselected range.

As further shown in FIG. 2, the activation switch 30 allows an operator to halt the flow of energy at any time, and thus functions as an electrical switch for the entire system. Although switch 30 is illustrated as mounted on trocar 24, it is understood that the switch may alternatively be located remote from the trocar, such as on a foot pedal (not shown).

In operation, the active electrode-obturator tip 42 delivers electrosurgical energy to the tissue 46 while the return electrode(s) 48 mounted on outer sheath member 34 receives the energy within the tissue by completing the circuit. This enhances the performance of the trocar as both the obturator tip 42 and the applied electrosurgical energy cooperate to penetrate and cauterize tissue simultaneously. The application of energy to tissue enhances the cutting performance of the obturator tip and also acts to cauterize tissue. This eliminates or reduces any bleeding associated with trocar use and accordingly reduces trauma.

The trocar construction of the present invention is also advantageous as it operates as a bipolar surgical instrument and requires no ground pad. This enables more effective and controlled application of electrosurgical energy with reduced risk of patient burning.

Virtually any generator able to provide electrosurgical energy for medical applications may be used with the present invention. Preferably, the generator 32 is a voltage determinative, low source impedance generator that provides radio frequency energy. A preferred generator is able to supply up to 3 amps of current and has an impedance value of less than 10 ohms.

The energy supplied by the generator 32 to the trocar 24 preferably is in the radio frequency (RF) range. Although virtually any frequency in the RF range may be supplied to trocar 24, the preferred range is about 500 to 700 KHz, and most preferably about 550 KHz.

Figure 4A:
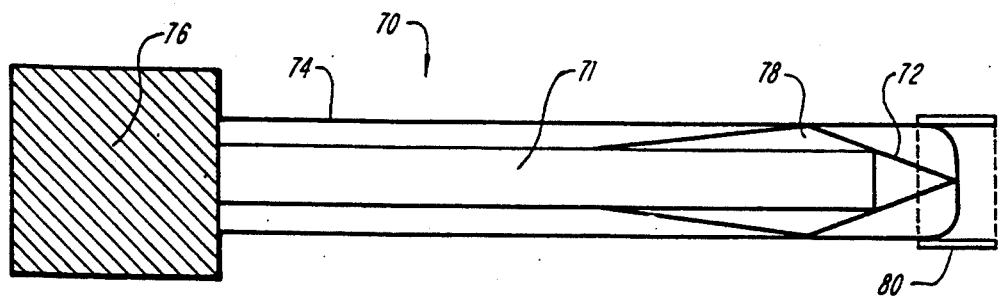
FIG. 4A schematically illustrates an alternative embodiment of a trocar device having a tissue penetrating electrode in a retracted position.
Figure 4B:
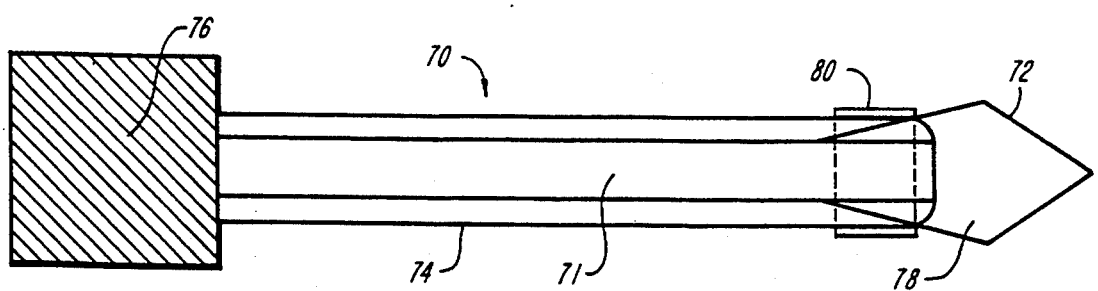
FIG. 4B schematically illustrates the trocar of FIG. 4A with the tissue penetrating electrode in an extended position.

FIGS. 4A and 4B illustrate a distal portion of an alternative embodiment of a trocar-like device 70. As illustrated, the device 70 includes a stylet 71 enclosed within an elongate hollow housing member 74. A distal portion of stylet 71 includes a spring electrode assembly 78 having a tissue penetrating edge 72 at its distal end. Block 76 simply illustrates that the device 70 is preferably connected to a handle and other selective operable features, as described above.

The tissue penetrating edge 72 and spring electrode assembly 78 from the active electrode used to deliver electrosurgical energy to the tissue. In this embodiment the active electrode may, for example, take the form of tip 42 as shown in FIG. 3. Similarly, the housing member 74 includes a return electrode (not shown) to form the inventive bipolar device described herein. The active electrode at the tissue penetrating edge 72 is electrically isolated from the return electrode disposed on the housing by any suitable arrangement, for example, as described above with respect to FIGS. 2 and 3. Moreover, the active electrode can comprise the entire surface area of the spring electrode assembly 78, or just a portion thereof.

FIG. 4A illustrates device 70 having spring electrode assembly 78 disposed within housing 74 in a retracted position. Spring electrode assembly 78 preferably is formed of or is coated with a medically compatible conductive material. Moreover, the assembly 78 is made of a pliable material or is otherwise biased to an expanded position. When retracted within housing 74, as shown in FIG. 4A, the assembly 78 is compressed. When the spring electrode assembly 78 is extended from housing 74, such as by actuation of stylet 71, the assembly 78 is free to expand to its natural configuration. As illustrated in FIG. 4B, the natural configuration of assembly 78 preferably is one where the diameter of spring electrode assembly 78 is greater than when it is compressed within housing 74.

This embodiment is advantageous because in the extended position the spring electrode assembly 78 has a greater surface area. Thus, the tissue penetrating edge 72 is able to contact more tissue and deliver more electrosurgical energy to the tissue than could safely be delivered with a more conventional tissue penetrating edge.

FIGS. 4A and 4B further illustrate that housing 74 can have a safety switch or shield 80. As illustrated the shield 80 is spring loaded and is biased to an extended position, as in FIG. 4A, in which it extends beyond the distal end of housing 74. The application of a compressive force to the distal end of shield 80 will cause the shield to slide rearwardly (as shown in FIG. 4B) to expose the distal end of housing 74 to tissue. When the force is removed from the distal end of shield 80, e.g., when the device 70 penetrates an internal barrier such as the abdomen, shield 80 returns to its extended position.

Preferably, shield 80 acts as a switch and is connected in circuit with the electrosurgical delivery electronics. When the shield 80 is in the extended position the flow of energy to tissue is prevented. However, when the shield 80 is in the retracted position energy is free to flow to tissue.

Thus, device 70 as described above is suitable for delivering electrosurgical energy to tissue in a trocar-like fashion. The device 70 can be further arranged to include impedance monitoring and power control electronics, as described with respect to FIGS. 2 and 3, to measure and control the flow of energy to the tissue based upon tissue impedance. The device 70 has the additional advantage of expanding the surface area contact of the active electrode to the target tissue during operation. This improves the delivery and flexibility of electrosurgery because tissue impedance is a function of the electrode's surface area, the distance between the electrodes, and the conductivity of the tissue, as well as the changes in tissue that result from heating.

It is understood that various modifications may be made to the invention described and claimed herein without departing from its intended scope. For example, the trocar-like devices described herein can also be constructed in a monopolar configuration, where the return electrode to an external generator is arranged externally to the device, such as through a ground pad. Furthermore, an activation switch, such as illustrated by item 30 in FIG. 2, is preferably arranged with each device constructed in accordance with the invention to improve patient safety while operating the device. A switch so constructed would enable the user to quickly and easily inhibit the power delivered to the patient. Also, the configuration of the electrodes formed at the tissue-penetrating edge and on the housing member can form a variety of shapes, including, for example, the conical tip shape illustrated in FIG. 2, or a pyramid shape, or a blunt tip, or as an annulus.

It is accordingly intended that all matters contained in the above description or shown in the accompanying drawings be interpreted as illustrative rather than in a limiting way.

What is claimed is:

1. A method for electrosurgically penetrating tissue, comprising the steps of:
   A. providing an electrosurgical tissue-penetrating probe having a stylet with an electrically conductive tissue penetrating edge at a distal end thereof adapted for delivering electrosurgical energy to adjacent tissue, the tissue-penetrating edge having spring means for increasing the diameter of the tissue-penetrating edge in contact with tissue when the tissue-penetrating edge is in the extended position and protrudes from the housing member, and the tissue-penetrating probe further having a return electrode disposed on a housing for the styler electrically isolated from the tissue penetrating edge of the stylet, the return electrode adapted to receive the electrical current delivered to the tissue by the edge; and
   B. delivering electrical energy to tissue adjacent the tissue penetrating edge of the stylet while forcing the stylet through the tissue.

2. A bipolar electrosurgical trocar system, comprising:
   an elongate hollow housing member having an open distal end and a return electrode associated with a tissue contacting portion of the distal end thereof;
   an elongate stylet, having at a distal end thereof an electrically conductive tissue-penetrating edge electrically isolated from the return electrode, the stylet adapted for axial movement within the housing member between an extended position in which the edge protrudes from the open distal end of the housing member, and a retracted position in which the edge is disposed within the housing member, the tissue-penetrating edge having spring means for increasing the diameter of the tissue-penetrating edge in contact with tissue when the tissue-penetrating edge is in the extended position and protrudes from the housing member;
   handle means, adjacent a proximal end of the housing member, for manipulating the trocar and for controlling axial displacement of the stylet;
   active current communication means associated with the trocar for communicating electrical energy through the trocar from a power source to the tissue-penetrating edge of the stylet for discharge through the edge to the tissue to be penetrated by the tissue-penetrating edge;
   return current communication means associated with the trocar for communicating the electrical energy delivered to the tissue by the tissue-penetrating edge from the return electrode to the power source;
   impedance measurement means, in circuit with the active communication means and return communication means, for measuring the electrical impedance of the tissue based upon the current within the tissue and generating a signal representative of tissue impedance; and
   a power control means, in circuit with the impedance measurement means and the remote power source, for regulating the electrosurgical energy delivered to the tissue from the tissue-penetrating edge in response to a signal from the impedance measurement means to maintain a measured tissue impedance to within a preselected range.

3. The bipolar electrosurgical trocar of claim 2, wherein the preselected range of the tissue impedance is preferably between 20–500 Ohms.

4. A monopolar electrosurgical tissue-penetrating device comprising:
   an elongate hollow housing member having an open distal end;
   an elongate stylet, having at a distal end thereof an electrically conductive tissue-penetrating edge electrically isolated from a remote electrode, the stylet adapted for axial movement within the housing member between an extended position in which the edge protrudes from the open distal end of the housing member, and a retracted position in which the edge is disposed within the housing member, the tissue-penetrating edge having spring means for increasing the diameter of the tissue-penetrating edge in contact with tissue when the tissue-penetrating edge is in the extended position and protrudes from the housing member:

handle means, adjacent a proximal end of the housing member, for manipulating the device and for controlling axial displacement of the stylet; and active current communication means associated with the device for communicating electrical energy through the device from a power source to the tissue-penetrating edge for discharge through the tissue-penetrating edge to the tissue to be penetrated by the edge.

5. A bipolar electrosurgical tissue-penetrating device, comprising:

an elongate hollow housing member having an open distal end and a return electrode associated with a tissue contacting portion of the distal end thereof;

an elongate stylet, having at a distal end thereof an electrically conductive spring electrode assembly having a tissue-penetrating edge and being electrically isolated from the return electrode, the stylet adapted for axial movement within the housing member between an extended position in which the spring electrode assembly expands to a diameter greater than its diameter within the housing member and protrudes from the open distal end of the housing member, and a retracted position in which the spring electrode assembly is confined within the housing member and is in a non-expanded condition;

handle means, adjacent a proximal end of the housing member, for manipulating the device and for controlling axial displacement of the stylet;

active current communication means associated with the device for communicating electrical energy through the device from a power source to the spring electrode assembly for discharge through the spring electrode assembly to the tissue to be penetrated by the tissue-penetrating edge; and return current communication means, associated with the device and electrically isolated from the active current communication means, for communicating the electrical energy from the current electrode to the power source.

6. The device of claim 5, further comprising a shield means for controlling the level of electrical energy from the spring electrode assembly to adjacent tissue, the shield means comprising an annular member slideably mounted upon a distal end of the housing and moveable between an extended position in which energy delivery is prevented and a retracted position in which energy delivery is permitted.

7. The device of claim 6 wherein the annular member is biased to the extended position.

* * * * *